(12) United States Patent (10) Patent No.: US 8,480,295 B2
Sarabi et al. (45) Date of Patent: Jul. 9, 2013

(54) METHOD AND DEVICE FOR TESTING THE FIRE HAZARD OF A MATERIAL

(75) Inventors: Bahman Sarabi, Krefeld (DE); Martin Behrendt, Meerbusch (DE)

(73) Assignee: UL LLC, Northbrook, IL (US)

( * ) Notice: Subject to any disclaimer, the term of this patent is extended or adjusted under 35 U.S.C. 154(b) by 766 days.

(21) Appl. No.: 12/339,710

(22) Filed: Dec. 19, 2008

(65) Prior Publication Data

US 2009/0168833 A1   Jul. 2, 2009

(30) Foreign Application Priority Data

Dec. 21, 2007 (DE) .......................... 10 2007 062 281

(51) Int. Cl.
*G01N 25/50* (2006.01)
*G01N 25/22* (2006.01)
*G01K 1/12* (2006.01)
*A62C 2/00* (2006.01)
*G08B 17/00* (2006.01)

(52) U.S. Cl.
USPC .................. 374/8; 169/60; 169/43; 374/120; 374/102; 374/141; 340/577

(58) Field of Classification Search
USPC ................ 348/207.99; 340/577, 578; 169/43, 169/60
See application file for complete search history.

(56) References Cited

U.S. PATENT DOCUMENTS 3,906,221 A * 9/1975 Mercier .................... 250/227.11
4,157,506 A * 6/1979 Spencer ....................... 307/653

(Continued)

FOREIGN PATENT DOCUMENTS

GB          1356023 A     6/1974
WO   WO-2004/086019 A1  10/2004

OTHER PUBLICATIONS

KR2001001224A "Device for inspectiing error in wafer . . . ", by Seo S R, Jan. 2001.*

(Continued)

*Primary Examiner* — Gail Verbitsky
(74) *Attorney, Agent, or Firm* — Marshall, Gerstein & Borun LLP; Michael P. Furmanek

(57) ABSTRACT

The invention relates to a method and a device for testing the fire hazard of a material. According to one embodiment of the method, a plane region of the surface of a specimen made of the material is brought in contact for at most a predetermined contact time with a glow wire, which has been heated to a predetermined temperature. Image data of the specimen are furthermore acquired by at least a first camera at least while the specimen is in contact with the glow wire. Image processing of the acquired image data of the specimen is furthermore carried out, preferably in realtime, ignition of the specimen by the glow wire being detected if applicable. A first duration is then determined, which corresponds to the length of time between the application of the tip of the glow wire on the specimen and the ignition of the specimen. Furthermore, according to one embodiment of the invention, a second duration may if applicable be determined by means of the image processing of the acquired image data of the specimen, the second duration corresponding to the length of time between the application of the tip of the glow wire on the specimen and the end of the ignition of the specimen. The method and the device are suitable in particular for carrying out tests to assess the fire hazard of materials according to the standards EN 60695-2-10, -12 and -13.

17 Claims, 4 Drawing Sheets

U.S. PATENT DOCUMENTS

| | | | | |
|---|---|---|---|---|
| 4,310,837 A | * | 1/1982 | Kornrumpf et al. | 340/598 |
| 4,567,347 A | | 1/1986 | Ito et al. | |
| 4,904,986 A | * | 2/1990 | Pinckaers | 340/578 |
| 6,245,576 B1 | * | 6/2001 | Hiley | 436/110 |
| 6,342,186 B1 | * | 1/2002 | Wingfield et al. | 422/241 |
| 6,909,066 B2 | | 6/2005 | Zheng et al. | |
| 7,348,562 B2 | * | 3/2008 | Irani | 250/339.02 |
| 7,843,352 B2 | * | 11/2010 | Hansen et al. | 340/577 |
| 2004/0060625 A1 | * | 4/2004 | Barbee et al. | 149/15 |
| 2005/0078732 A1 | * | 4/2005 | de Ris et al. | 374/29 |
| 2006/0115154 A1 | | 6/2006 | Chen | |
| 2006/0133445 A1 | * | 6/2006 | Lyon | 374/8 |
| 2007/0048682 A1 | | 3/2007 | Bartel et al. | |
| 2009/0234051 A1 | * | 9/2009 | Endtner et al. | 524/133 |
| 2010/0025582 A1 | * | 2/2010 | Weil | 250/332 |
| 2010/0179258 A1 | * | 7/2010 | Sakata | 524/101 |

OTHER PUBLICATIONS

Zwick GMBH & Co. KG, "Using the Glow Wire test to reduce fire hazards," Internet Citation: URL: http://www.zwick.co.uk/images, retrieved Dec. 6, 2006, 3 pages.

PTL Dr. Grabenhorst GMBH: "Glow-Wire Test," Internet Article: URL: http://www.vandentempel.com, retrieved Jun. 2, 2009, 6 pages.

International Standard, "Fire hazard testing—Part 2-12: Glowing/hot-wire based test methods-Glow-wire flammability test method for materials," Internet Article, 2000, 7 pages.

International Search Report for Application No. PCT/EP2008/010511 dated Jun. 8, 2009.

Written Opinion for Application No. PCT/EP2008/010511 dated Jun. 21, 2010.

International Preliminary Report on Patentability for Application No. PCT/EP2008/010511 dated Jun. 22, 2010.

Figure 2:
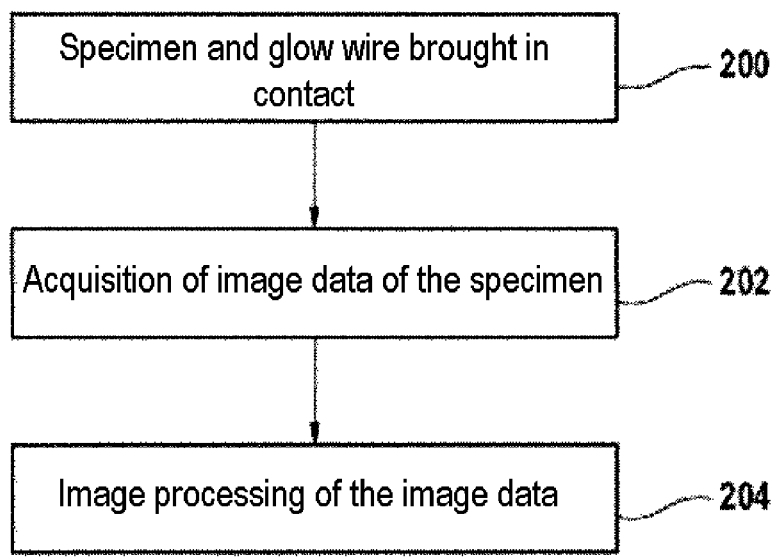

IEC, "Fire Hazard Testing," 60695-11-20, Edition 1.1, (Aug. 2003), pp. 23-27, Figure 2 (p. 31), p. 37.

Figure 1:
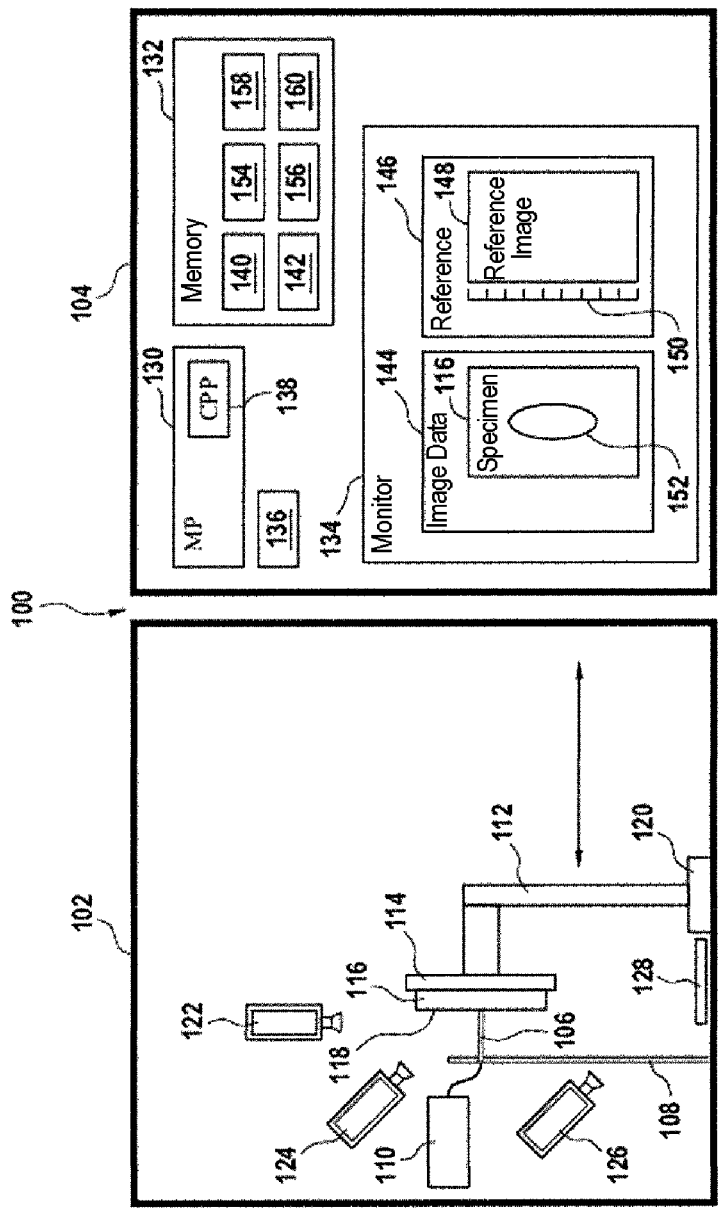
Figure 3:
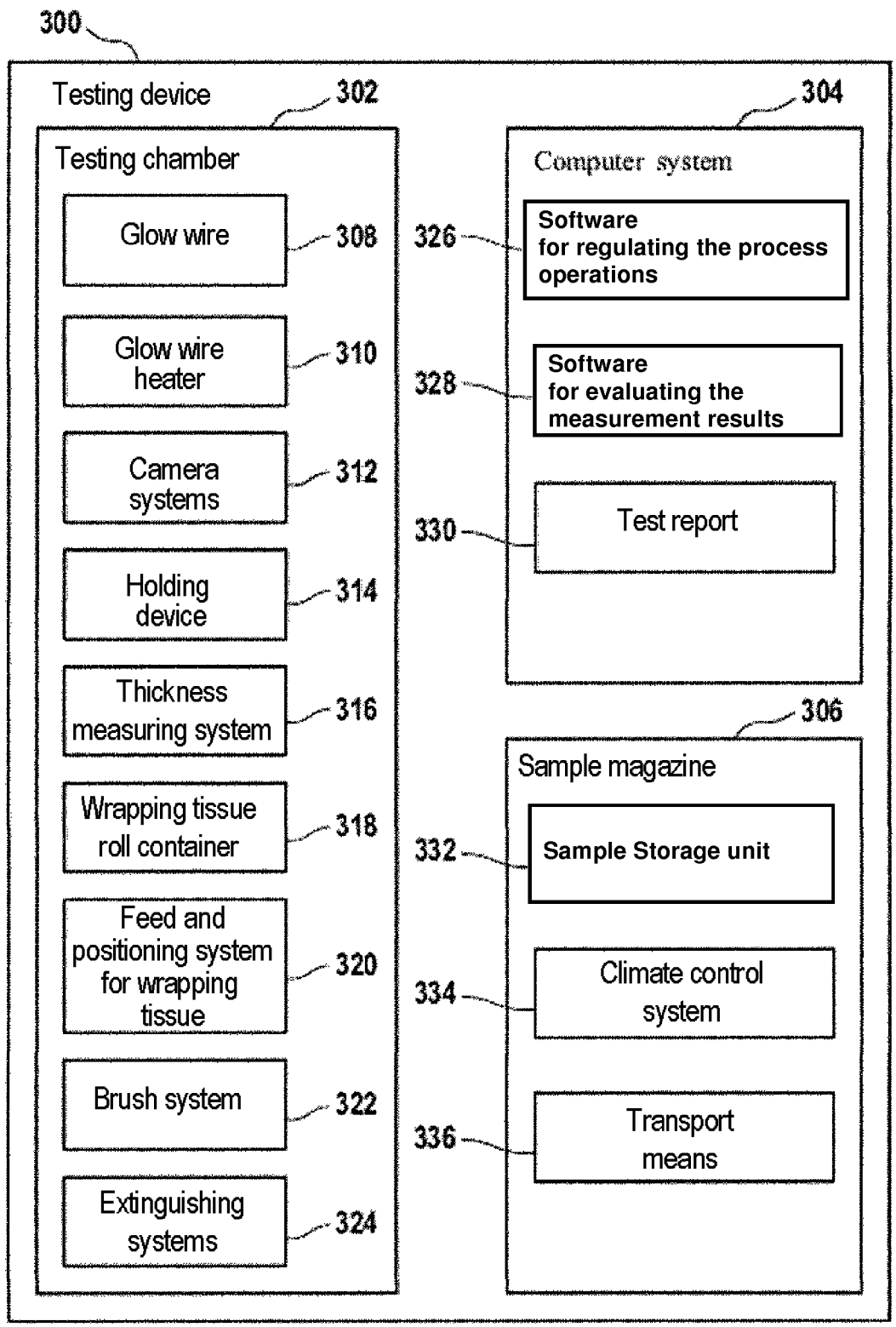

IEC, "Fire Hazard Testing," 60695-11-10, Edition 1.1 (Aug. 2003), pp. 27-33, Figure 3 (p. 39), p. 49, pp. 23-26, Figure 1 (p. 35) and p. 47.

DIN IEC 695-2-1 VDE 0471-2-1:Mar. 1984 Prüfungen zur Beurteilung der Brandgefahr-Prüfverfahren 2-1: Prüfung mit dem Glühdraht und Anleitung (VDE-Bestimmung), Deutsche Normen. Din Norm (1984). Retrieved from the Internet: URL:http://www.vde-verlag.de/normen/0471001/din-iec-695-2-Letter 1-vde-0471-2-1-1984-03.html.

Examination Report for Application No. EP08863638.6, dated Jun. 25, 2012.

European Communication for Application No. 08 863.638.6 dated Apr. 10, 2012.

Messori et al., "Flame retarding poly (methyl methacrylate) with nanostructured organic-inorganic hybrids coatings," Polymer, vol. 44, pp. 4463-4470, 2003.

English translation of sections 1-12 on pp. 4-6 of DIN IEC 695-2-1 VDE 0471-2-1:Mar. 1984 Prüfungen zur Beurteilung der Brandgefahr-Prüfverfahren 2-1: Prüfung mit dem Glühdraht und Anleitung (VDE-Bestimmung), Deutsche Normen. Din Norm (1984), retrieved from the Internet: URL:http://www.vde-verlag.de/normen/0471001/din-iec-695-2-1-vde-0471-2-1-1984-03.html, and which was cited in the Second Supplemental Information Disclosure Statement submitted on Sep. 4, 2012 in this application.

* cited by examiner

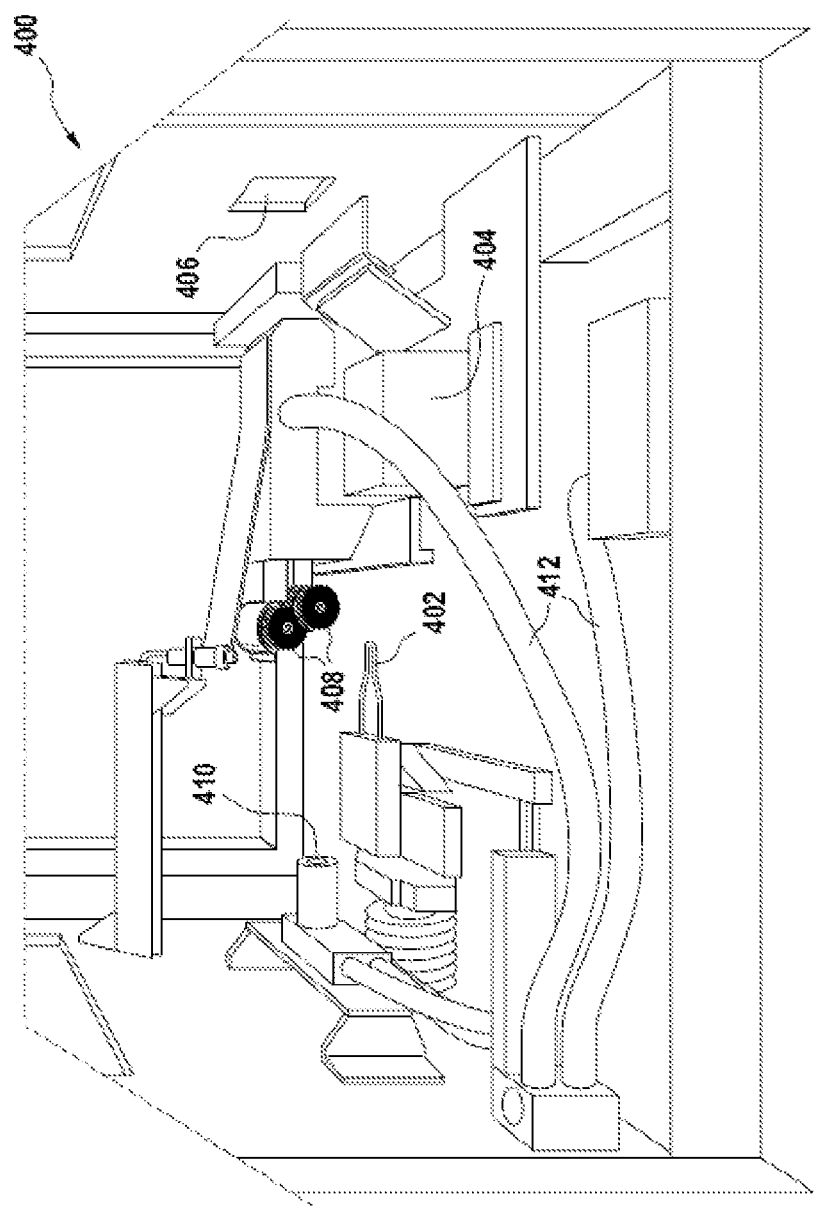

METHOD AND DEVICE FOR TESTING THE FIRE HAZARD OF A MATERIAL

The invention relates to a method and a device for testing the fire hazard of a material.

Materials are solid substances, such as metals or plastics. Materials, in particular plastics, form constituents of electrical engineering equipment. For example, plastics are used as insulation for electrical cables. In electrical engineering equipment, the materials may experience excessive exposure to heat by electrical processes. For example, a current flowing through a copper cable leads to the heating of the copper, so that the plastic insulation enclosing the copper cable is also heated. Under certain conditions furthermore, for example when a fault current flows through a cable and components are therefore overloaded and faulty connections are created, certain components of electrical engineering equipment reach a temperature which is sufficient to ignite parts in their vicinity.

When materials are used in electrical engineering equipment, the combustion properties of the materials being used should therefore be known in order to prevent such electrical engineering equipment from igniting relatively easily.

The standards EN 60695-2-10, -12, -13 specify test methods for simulating the effect of the exposure to heat which can be generated by heat sources such as glowing parts or temporarily overloaded electrical resistors in electrical engineering equipment, and in order to be able to assess the fire hazard of materials by a simulation method.

In particular, the standard EN 606952-10 specifies a glow wire test apparatus, by means of which testing of the various materials is to be carried out.

According to this standard, the glow wire test apparatus comprises a glow wire, which consists of a loop of resistor wire that is electrically heated to a set temperature. The tip of the glow wire is brought in contact with the specimen made of the material for a set time, and a range of observations and measurements are carried out, these depending on the particular test method as described in the standard Norm EN 60695-2-12 or in the standard EN 60695-2-13.

The standard EN 60695-2-12 specifies the details for testing with the glow wire, which is carried out as a flammability test to determine the glow wire flammability index (GWFI) of specimens made of solid electrical insulating materials or other solid materials. The test results allow relative comparison of various materials according to their ability to extinguish flames after the heated glow wire is removed, and their ability not to produce burning or glowing particles which may entail fire spreading to a specified layer of wrapping tissue arranged below them.

The standard EN 60695-2-13 specifies the details for testing with the glow wire, which is carried out as an ignitability test to determine the glow wire ignition temperature (GWIT) of specimens made of solid electrical insulating materials or other solid materials. The test results allow relative comparison of various materials by measuring the temperature at which the specimen ignites during the application of the electrically heated glow wire as an ignition source.

Methods for testing the fire hazard of materials, as described for example in the European standards mentioned above, are carried out according to the prior art by staff who manually perform the process steps described in the standards. It is however clear that a test method carried out by individuals to assess the fire hazard of a material is also dependent on subjective person-specific influences.

It is therefore an object of the invention to provide an improved method for testing the fire hazard of a material. It is also an object of the invention to provide an improved device for testing the fire hazard of a material.

The objects of the invention are achieved by the features of the independent claims. Embodiments of the invention are specified in the dependent claims.

In a first aspect, the invention relates to a method for testing the fire hazard of a material. According to one embodiment of the invention, a plane region of the surface of a specimen is brought in contact with a glow wire for a predetermined contact time. The specimen consists of the material to be tested. During the contact time, a tip of the glow wire is applied approximately on the middle of the plane region, the glow wire having previously been heated to a predetermined temperature. In a further method step, image data of the specimen are acquired with at least a first camera at least while the specimen is in contact with the glow wire. Image processing of the acquired image data of the specimen is furthermore carried out, ignition of the specimen by the glow wire being detected if applicable. A first duration is determined, the first duration corresponding to the length of time between the application of the tip of the glow wire on the specimen and the ignition of the specimen.

According to this embodiment, image data of the specimen are acquired by the first camera at least during the time when the specimen is in contact with the glow wire, these image data being processed by the image processing and used to detect a flaming specimen. Subjective influences, which staff may have when assessing whether the specimen has ignited, therefore no longer occur here.

According to one embodiment of the invention, the first duration is stored. Image processing of the acquired image data of the specimen is furthermore carried out, an end of the ignition of the specimen being detected after a second duration if applicable, the second duration corresponding to the length of time between the application of the tip of the glow wire on the specimen and the end of the ignition of the specimen. If applicable, the second duration is also stored.

According to one embodiment of the invention, the contact between the specimen and the glow wire is ended after a predetermined contact time has elapsed. The acquisition of image data of the specimen by the at least first camera is however also continued for a predetermined observation time after the contact time has elapsed, for example for 30 seconds, as specified in EN 60695-2-12.

According to one embodiment of the invention, the ignited specimen is extinguished either after the ignition has been detected or after the observation time has elapsed. In order to extinguish the ignited specimen, for example, nitrogen nozzles are used through which nitrogen is blown onto the ignited specimen, which leads to the flames being extinguished. The ignited specimen is blown with nitrogen through the nitrogen nozzles for a predetermined and adjustable extinguishing time.

According to one embodiment of the invention, the specimen is counted as being ignited only if flaming of the specimen is detected by the image processing of the image data for at least a predetermined flaming time.

For example, the standard EN 60695-2-13 describes that the ignition must be visible for at least 5 seconds. Visibility of the ignition may be defined by corresponding criteria in the image processing. The use of automated image processing to determine the first duration, which is a measure of the instant when the specimen flames, and to determine the second duration which is a measure of the extinguishing of the flames of the specimen, therefore also make it possible to check whether the ignition of the specimen has persisted for at least the predetermined flaming time. This criterion can be implemented very accurately by using the image processing, since subjective influences no longer play a role.

According to one embodiment of the invention, image processing of the image data of the specimen is used to detect whether burning threads are pulled from the specimen at the end of the contact with the glow wire and whether the burning threads ignite the specimen. If applicable, the burning threads on the glow wire are then extinguished. The possibility of recognizing threads, which are formed when the specimen is separated from the glow wire, is important since burning threads can ignite more easily on the glow wire than the specimen per se can, and these burning threads can set the specimen on fire. This should not, however, be interpreted as ignition of the specimen.

According to one embodiment of the invention, the glow wire is cleaned with a brush system. Cleaning the glow wire is important in particular when threads have formed on the glow wire, and these are removed by the cleaning.

According to one embodiment of the invention, the region of the specimen, where the glow wire is located, is not employed by the image processing in order to determine whether the specimen is burning. In particular, the glow wire is filtered out of the acquired image data. Flaming of the specimen is thus detected by means of the image processing outside the region where the glow wire is located, which avoids the likelihood of false detection due to the glowing wire being falsely interpreted as a burning specimen.

According to one embodiment of the invention, the glow wire detected by the image processing is recognized as such. The glowing of the wire is therefore not mistakenly interpreted as a burning specimen.

According to one embodiment of the invention, the acquired image data of the specimen are respectively compared with a reference image of the specimen, differences in the brightness between the image data and the reference image being used to detect ignition of the specimen. For example, the first camera may be a black-and-white camera by which a reference image of the non-flaming specimen has been acquired in the test position, under the light conditions which prevail during the actual test. An integral brightness, or the luminosity coming from the reference image, may thus be measured for the reference image. The setpoint value determined in this way is then compared with the actual value of the brightness, which is determined from the currently acquired image data of the specimen. If the actual value differs from the setpoint value by more than a predetermined threshold value, then this is an indication that the specimen is ignited. The threshold value depends on the camera system being used, the sample and the ambient brightness. The threshold value is preferably determined experimentally. To this end the integral brightness value of a non-flaming sample (reference) and the integral brightness value of a flaming sample are determined with the aid of the acquired images of a non-flaming sample and a flaming sample. The threshold value lies above the value of the integral brightness of the non-flaming sample and below the value of the integral brightness of the flaming sample. For example, the geometric or arithmetic mean of the values of the integral brightness for the non-flaming sample and for the flaming sample may be used as a threshold value.

Measurement of the integral brightness and comparison between the setpoint and actual values has the advantage that relatively little computing power is needed for this, and it is therefore possible to detect ignition of the specimen essentially in realtime.

According to one embodiment of the invention, the acquired image data of the specimen are compared with a reference image of the specimen, and ignition of the specimen is detected if the colours of at least parts of the specimen are different from the corresponding colours of the parts in the reference image.

The at least first camera is for example a colour camera, so that the image data of the specimen comprise colour information for each acquired pixel. The reference image may for example have been taken from a non-ignited specimen of the same material and with the same geometrical dimensions, and with the same light conditions as prevail when testing the fire hazard of the specimen. By comparing the colours of the acquired image data of the specimen with the corresponding colours in the reference image, ignition of the specimen can therefore be detected.

According to one embodiment of the invention, for each pixel in the acquired image data of the specimen, the colours are compared with the colours of the corresponding pixel in the reference image. If the colour of the pixel in the image data differs from the colour of the pixel in the reference image, then this is an indication that the specimen has ignited at the position corresponding to the pixel.

According to one embodiment of the invention, the connected pixels in the acquired image data, the colour of which differs from the corresponding pixels in the reference image, are used in order to detect ignited parts of the specimen. Thus, the region of the specimen which is ignited can be detected by a continuous region of pixels differing in its colour from the corresponding pixels in the reference image.

According to one embodiment of the invention, the colour for each pixel of the image data is determined according to the RGB colour model or according to the CMYK colour model. For example, three tristimulus values are determined according to the RGB model for each pixel. The first tristimulus value reflects the red component, the second tristimulus value reflects the green component and the third tristimulus value reflects the blue component in the colour. The colour of the pixel in the image data is compared with the corresponding colour of the corresponding pixel in the reference image, by comparing at least one of the tristimulus values with the corresponding tristimulus value of the colour in the reference image. If the two tristimulus values differ from one another by more than a predetermined threshold value, then this is regarded as an indication that the specimen has ignited at the position corresponding to the pixel. The threshold value depends on the camera system being used, the sample and the ambient conditions, for example the illumination. The threshold value is preferably determined experimentally. To this end the tristimulus value of a non-ignited sample (reference) and the tristimulus value of an ignited sample are determined with the aid of the acquired images of a non-ignited sample and an ignited sample. The threshold value lies between the tristimulus values of the non-ignited sample and the ignited sample. For example, the geometric or arithmetic mean of the values of the tristimulus values for the non-ignited sample and for the ignited sample may be used as a threshold value.

According to one embodiment of the invention, the height of the flames of the ignited specimen may be determined by the image processing of the acquired image data of the ignited specimen. The height of the flames is furthermore stored.

According to one embodiment of the invention, the acquired image data of the specimen are furthermore compared with a reference image of the specimen. The reference image comprises a measurement scale, the height of the flames of the ignited specimen being determined by means of the measurement scale. The region in which the specimen is ignited, or the region in which the specimen gives off flames, can be determined using the image data by comparing the acquired image data with the reference image, as described above. According to this embodiment, the reference image furthermore has a measurement scale so that the height of the flames can be determined by means of the measurement scale.

According to one embodiment of the invention, wrapping tissue is positioned in a region, the glow wire and the specimen coming in contact above the region. The image data of the wrapping tissue are furthermore acquired with at least a second camera at least while the specimen is in contact with the glow wire. Image processing of the acquired image data of the wrapping tissue is furthermore carried out, ignition of the wrapping tissue being detected if applicable, a third duration being determined which corresponds to the length of time between the application of the tip of the glow wire on the specimen and the ignition of the wrapping tissue. If applicable, the third duration is stored and the flaming wrapping tissue is extinguished. The third duration is used to classify the specimen, or the material of which the specimen consists, according to the standard EN 60695-2-13.

According to one embodiment of the invention, the specimen and the glow wire are pressed against one another with a predetermined force. For example, the glow wire is fixed and the specimen is moved on a carriage in the direction of the glow wire. A force transducer is arranged on the carriage, so that the force with which the specimen is pressed against the glow wire can be adjusted according to the predetermined force. The force transducer may furthermore be used in order to trigger the start point for the predetermined contact time. As soon as the predetermined force acts between the glow wire and the specimen, which is measured by the force transducer, the predetermined contact time starts to run.

According to one embodiment of the invention, a penetration depth of the glow wire through the specimen is furthermore determined. The penetration depth is furthermore stored. The penetration depth may for example be determined by equipping the aforementioned carriage with means for measuring the distance traveled, which record the length traveled from the time when the predetermined force (1.0 N±0.2 N according to the standards indicated above) acts, and for as long as it acts, which corresponds to the penetration depth of the glow wire through the specimen.

According to one embodiment of the invention, the temperature of the glow wire is regulated to the predetermined temperature before the glow wire comes in contact with the specimen. The temperature regulation is furthermore switched off during the contact between the glow wire and the specimen.

According to one embodiment of the invention, the temperature of the glow wire is determined by an optical temperature measurement system. Using an optical temperature measurement system in order to measure the temperature of the glow wire has the advantage that rapid and contactless temperature measurement is thereby possible. As already mentioned above, the glow wire is cleaned by means of brushes to remove residues of a specimen remaining on the glow wire. Since the optical temperature measurement system is not directly in contact with the glow wire, the temperature measurement system is not damaged or worn by the cleaning process. A pyrometer may be mentioned as an example of an optical temperature measurement system. Other temperature measurement systems, which are based on measuring the infrared spectrum of the IR light emitted by the glow wire, are furthermore suitable for measuring the temperature of the glow wire.

According to one embodiment of the invention, a multiplicity of specimens made of the material are kept in a storage unit, a specimen respectively being taken from the storage unit and brought to the glow wire.

According to one embodiment of the invention, the thickness of the specimen is measured and the thickness of the specimen is stored, before the specimen is brought in contact with the glow wire.

According to one embodiment of the invention, the specimens are designed in the form of a disc or plate. This has the advantage that the specimens can be transported particularly easily from the storage unit into a testing device, in which the fire hazard of the specimens is tested, since the specimens are particularly easy to handle owing to their geometry. Furthermore, the standards mentioned above stipulate that the specimens should be designed in the form of a plate or disc.

According to one embodiment of the invention, a holding device is used for bringing the specimen to the glow wire, the specimen being fixed with a surface essentially aligned horizontally while coming from the storage unit, the holding device having a tilting mechanism, the holding device being tiltable essentially through 90° by the tilting mechanism and the surface with the plane region essentially being aligned vertically by the tilting of the holding device.

According to one embodiment of the invention, the holding device can be moved and/or tilted with a predetermined speed. For example, the holding device can be moved with a speed of between 10 and 25 mm/sec., as intended by the standards mentioned above, when the specimen is being moved toward the glow wire.

According to one embodiment of the invention, the method is carried out for a plurality of specimens with temperatures specified in the standard EN 60695-2-12:2001 or EN 60695-2-13:2001 for the glow wire, the glow wire flammability index being determined for the specimens according to EN 60695-2-12:2001 or the glow wire ignition temperature being determined for the specimens according to EN 60695-2-13:2001.

In another aspect, the invention relates to a computer program product having computer-executable instructions for carrying out and regulating steps of the method according to the invention.

In another aspect, the invention relates to a device for testing the fire hazard of a material.

Preferred embodiments of the invention will be explained in more detail below with reference to the drawings, in which:

FIG. 1 shows a block diagram of a device for carrying out a test of the fire hazard of a material, FIG. 2 shows a flow chart, which represents steps of the method according to the invention, FIG. 3 shows a block diagram of a testing device, FIG. 4 shows an image of an embodiment of a testing chamber.

FIG. 1 shows a block diagram of a device 100 for carrying out a test of the fire hazard of a material. The device 100 comprises a testing chamber 102 and a computer system 104. The testing chamber 102 comprises a glow wire 106. The glow wire 106 is held by a frame 108, which is installed in a fixed fashion. The glow wire 106 is designed in the form of a loop, as for example described in detail in the European standard EN 60695-2-10, the cross section of the glow wire loop essentially being aligned horizontally. The glow wire 106 can be heated to a predetermined temperature by a glow wire heater 110.

The testing chamber 102 furthermore comprises a holding device 112. The holding device 112 can be moved along the arrow directions with a particular predetermined and adjustable speed. The holding device 112 comprises means 114 for fixing a specimen 116.

The specimen 116 is designed in the form of a plate and has a surface 118 with a plane region. The holding device 112 is designed so that the specimen 116 can be fixed on the fixing means 114 in such a way that the plane region of the surface 118 can be brought approximately centrally in contact with the tip of the glow wire 106. The holding device 112 in this case moves in the direction of the glow wire tip and presses the specimen 116 against the glow wire with a predetermined force, for example 1.0 N±0.2 N. In order to measure the force with which the specimen 116 is pressed against the glow wire tip, there is for example a force and displacement measuring system 120 in the lower region of the holding device 112, which measures the force. The force and displacement measuring system 120 furthermore measures the distance which the holding device travels after contact with the glow wire 106. This distance corresponds to the penetration of the glow wire 106 through the specimen 116.

The testing chamber 102 furthermore comprises the camera systems 122, 124 and 126. The camera system 122 is used to record the glow wire 106. The camera system 124 is used to record the specimen 116. The camera system 126 is used to record wrapping tissue 128, which is positioned below the region in which the glow wire 106 and the specimen 116 come in contact.

The computer system 104 comprises a microprocessor 130, a memory 132, a monitor 134 and interfaces for the camera systems 122, 124 and 126. The microprocessor 130 runs a computer program 138, which is used to control and regulate the process sequences described below in the testing chamber 102 and to evaluate the measurement results obtained experimentally in the testing chamber.

As already mentioned above, the holding device 112 can be moved in the direction of the glow wire 106. Before the specimen 116 comes in contact with the glow wire 106, however, the holding device 112 is positioned so that the specimen 116 lies a certain distance away from the glow wire 106, for example 100 mm. The computer program product 138 controls the glow wire heater 110 so that it heats the glow wire 106 to a predetermined temperature 140, which is stored in the memory. The temperature 140 is, for example, one of the testing temperatures which are specified in the standards EN 60695-2-12 or -13 (500° C., 550° C., 600° C., 650° C., 700° C., 750° C., 800° C., 850° C., 900° C., 960° C.). The temperature 140 may, for example, be selected from the values specified in the standards so that it is adapted to the material of which the specimen 116 consists.

In order to regulate the temperature 140, the camera system 122 is furthermore used which supplies infrared images of the glow wire to the computer system 104. The glow wire 106 consists for example of a nickel-chromium compound, for which the infrared spectrum as a function of temperature is known. The computer program product 138 can therefore use the images of the glow wire loop delivered by the camera system 122 to determine the IR spectrum emitted by the heated glow wire 106, and with the aid of this it can determine the current temperature of the glow wire 106. With knowledge of the current temperature of the glow wire 106, the glow wire heater 110 can be regulated accordingly.

The camera system 122 may comprise a pyrometer, which internally measures the temperature of the glow wire 106. The pyrometer may be a one-colour or two-colour pyrometer. The actual value of the temperature, delivered by the pyrometer, can therefore be input into a control path built directly into the glow wire heater 110, by means of which the temperature of the glow wire is adjusted to the setpoint temperature 140.

Furthermore, as an alternative to the camera system 122, it is also possible to use a thermocouple wire which is located in a bore of the glow wire tip in order to measure the temperature of the glow wire 106.

When the glow wire 106 is at the required temperature 140, the glow wire heater 110 is switched off and the holding device 112 is moved in the direction of the glow wire 106, as described above, until the specimen 116 is in contact with the tip of the glow wire 106. The computer program product 138 regulates the position of the holding device 112 so that the contact between the specimen and the glow wire lasts for at most a predetermined contact time 142, for example 30 seconds according to the standards mentioned above. The contact time 142 is stored on the memory 132. As already mentioned above, the holding device 112 contains a force and displacement measuring system 120 which is used to ensure that the specimen 116 is pressed onto the glow wire 106 with a predetermined force (1 N). The instant from which the contact time 142 starts to run can therefore be defined by means of the instant at which the specimen 116 is for the first time pressed onto the glow wire 106 with the predetermined force.

At least for the time during which the specimen 116 is in contact with the glow wire 106, via one of the interfaces 136 the camera system 124 delivers image data 144 of the specimen 116, which are represented on the monitor 134.

The computer program product 138 processes the image data 144, for example in realtime, so that ignition of the specimen 116 by the glow wire 106 is detected. For example, the image data 144 of the specimen 116 are compared with a reference 146, the reference 146 comprising a reference image 148 of the specimen 116 and a measurement scale 150. The reference image 148 of the specimen 116 is, for example, an image which has been acquired by the camera system 124 with the same type of light conditions from the specimen in the testing chamber 102, without the glow wire 106 being heated. The measurement scale 150 has been positioned on the left of the specimen during the recording.

By the image processing of the image data 144, the computer program product 138 can detect ignition of the specimen by the glow wire. To this end, for example, the integral brightness of the specimen 116 in the image data is compared with the corresponding integral brightness of the reference image. If the integral brightness of the specimen in the image data 144 exceeds the integral brightness of the reference image by more than a predetermined threshold value, then this is an indication that the specimen 116 has ignited. In this case, it is sufficient for the camera system 124 to be a black-and-white camera. The threshold value depends on the camera system being used, the sample and the ambient brightness. The threshold value is preferably determined experimentally. To this end the integral brightness value of a non-ignited sample (reference) and the integral brightness value of an ignited sample are determined with the aid of the acquired images of a non-ignited sample and an ignited sample. The threshold value lies above the value of the integral brightness of the non-ignited sample and below the value of the integral brightness of the ignited sample. For example, the geometric or arithmetic mean of the values of the integral brightness for the non-ignited sample and for the ignited sample may be used as a threshold value.

As an alternative, the currently obtained image of the specimen 116 may be analysed pixel-by-pixel via the computer program product 138. For each pixel, the colour may for example be determined according to the RGB colour model or according to the CMYK colour model. The colour of the pixel in the specimen 116 can then be compared with the corresponding colour of the pixel in the reference image 148. If the colours of the pixel in the specimen and of the corresponding pixel in the reference image differ from one another by more than a predetermined threshold value, then this is an indication that the specimen has ignited at the position corresponding to the pixel.

Thus, for example, a region 152 of connected pixels may be identified by the computer program product 138, each pixel in the region 152 differing in its colour from the corresponding pixel in the reference image 148 by more than a predetermined threshold value. The region 152 is therefore identified as the region of the specimen 116 in which the specimen is burning. The flame height 154 can furthermore be identified by measuring the region 152 against the measurement scale 150. The flame height 154 is then stored in the memory 132 by the computer program product 138. This may be done for each image 144 which is delivered by the camera system 124.

The threshold value depends on the camera system being used, the sample and the ambient conditions, for example the illumination. To this end the tristimulus value of a non-burning sample (reference) and the tristimulus value of a burning sample are determined with the aid of the acquired images of a non-burning sample and a burning sample. The threshold value lies between the tristimulus values of the non-burning sample and the burning sample. For example, the geometric or arithmetic mean of the values of the tristimulus values for the non-burning sample and for the burning sample may be used as a threshold value.

If it is found through the image processing by the computer program product 138 that the specimen 116 is ignited, then a first duration 156 is determined. The first duration 156 corresponds to the difference between the instant at which it was discovered that the specimen is burning, and the instant at which the tip of the glow wire was applied on the specimen 116. The computer program product 138 can furthermore determine via the image processing of the image data 144 whether the ignition of the specimen is extinguished, and if applicable establish a second duration 158 which corresponds to the duration between the extinguishing of the specimen and the instant when the tip of the glow wire is applied onto the specimen.

At the latest after the predetermined contact time 142 has elapsed, the contact between the specimen 116 and the glow wire 106 is separated and the specimen is positioned by means of the holding device 112, for example at a distance of 100 mm from the glow wire 106, so that the specimen 116 is no longer affected by the glow wire. The specimen 116 is in this case observed by the camera system 124 for a predetermined observation time 160, which is stored on the memory 132. The predetermined observation time 160 is, for example, 30 seconds according to the standard EN 60695-2-12. Extinguishing of the specimen may also be detected during this time.

As already mentioned above, wrapping tissue 128, which may for example be positioned on a wooden board, is located below the region in which the glow wire 106 comes in contact with the specimen 116. The wrapping tissue 128 is observed by the camera system 126, which delivers image data to the computer system 104. With the aid of the image data 104, the computer program product 138 can determine whether the wrapping tissue 128 is burning. For example, a reference image of the non-burning wrapping tissue 128 may be stored on the computer system 104, which is compared with the current image delivered by the camera system 126. If the integral brightness of the current image differs from the reference image of the wrapping tissue by more than a predetermined threshold value, then this is regarded as an indication that the wrapping tissue 128 is burning. The threshold value depends on the camera system being used, the composition of the wrapping tissue and the ambient brightness. The threshold value is preferably determined experimentally. To this end, the integral brightness value of a non-burning wrapping tissue and the integral brightness value of a burning wrapping tissue are determined with the aid of the acquired images of a non-burning wrapping tissue and a burning wrapping tissue. The threshold value lies above the value of the integral brightness of the non-burning wrapping tissue and below the value of the integral brightness of the burning wrapping tissue. For example, the geometric or arithmetic mean of the values of the integral brightness for the non-burning wrapping tissue and for the burning wrapping tissue may be used as a threshold value. Burning wrapping tissue 128 serves as an indicator that burning parts have fallen off the specimen 116, and have led to ignition of the wrapping tissue 128.

The device 100 may be used to test the fire hazard of a material according to the standard EN 60695-2-13. To this end, a series of measurements is carried out with a plurality of specimens, one of the tested temperatures cited in this standard being used for a first specimen. If ignition of the specimen is found while the first specimen is in contact with the glow wire 106 heated to the corresponding temperature, the contact between the glow wire and the specimen is ended and the first specimen is extinguished. The duration until ignition (cf. first duration 156), i.e. the time from the start of the application of the tip of the glow wire until the instant at which the first specimen ignites, is recorded. Next, for a new second specimen, a test is made to determine whether it still ignites at a reduced temperature. The amount by which the original temperature of the glow wire 106 is reduced is stipulated in the standard.

Correspondingly, the glow wire temperature for the second specimen is increased if the first specimen has not heated at that the temperature which was set. It is thus possible to determine the highest testing temperature which does not cause ignition of the specimens during three successive tests. The testing temperature, which is 25 Kelvin (or 30 Kelvin between a glow wire temperature of 900° C. and 960° C.) more than the highest testing temperature, is referred to according to the aforementioned standard as the glow wire ignition temperature (GWIT). The glow wire ignition temperature, as well as the time until ignition which occurs at the next testing temperature up for the specimens, is displayed in a test report, for example on the monitor 134.

The device is furthermore suitable for testing the fire hazard of a material on specimens according to the standard EN 60695-2-12. In this case, as described above, the testing is carried out for a plurality of specimens and the time (cf. first duration 156) from the start of the application of the tip of the glow wire until the instant at which a specimen 128 or the wrapping tissue arranged on it ignites, or the duration (cf. second duration 158) from the start of the application of the tip until the instant at which the flames are extinguished, during or after the application time until the predetermined observation time of 30 seconds has elapsed. According to this standard, the glow wire flammability index (GWFI) is determined, which corresponds to the highest testing temperature at which the conditions a) and b) mentioned below are satisfied during three successive tests on different specimens. Condition a) specifies that the flames or glowing on the specimen must be extinguished within 30 seconds after removal of the glow wire, and condition b) specifies that there must be no ignition of the wrapping tissue. The over the measurements carried out on the specimens may furthermore be used to generate a test report, as is described in the standard.

According to the embodiment described above, the glow wire 106 is fixed and the specimen 116 is moved by means of the holding device 112. It is however readily clear to the person skilled in the art that, as an alternative to this, the specimen 116 may be held fixed and the glow wire 106 may be mounted in a mobile fashion. The force and displacement of measuring system may in this case also be arranged on the frame 108. As an alternative, the force and displacement measuring system may be embodied using two separate components, a displacement measuring system being arranged for example on the mobile frame 108 of the glow wire and the force measuring system being arranged on the holding device 112, in order to measure the application force of the glow wire 106 on the specimen 118 in the event of contact.

FIG. 2 shows a flow chart which represents steps of the method according to the invention for testing the fire hazard of a material. According to step 200 of the method according to the invention, the plane region of the surface of a specimen is brought in contact with a glow wire for at most a predetermined contact time, the specimen consisting of the material, a tip of the glow wire being applied approximately on the middle of the plane region, and the glow wire being at a predetermined temperature. According to step 202 of the method according to the invention, image data of the specimen are acquired with at least a first camera at least while the specimen is in contact with the glow wire. According to step 204 of the method according to the invention, image processing of the acquired image data of the specimen is carried out. Ignition of the specimen by the glow wire is detected if applicable, a first duration being determined, the first duration corresponding to the length of time between the application of the tip of the glow wire on the specimen and the ignition of the specimen.

FIG. 3 shows a block diagram of a testing device 300 having a testing chamber 302, a computer system 304 and a sample magazine 306. The testing chamber 302 comprises a glow wire 308 and a glow wire heater 310 for heating the glow wire 308 to a predetermined temperature. The testing chamber 302 furthermore comprises camera systems 312, a holding device 314 and a thickness measuring system 316. The testing chamber 302 furthermore comprises a wrapping tissue roll container 318 and a feed and positioning system for wrapping tissue 320. The testing chamber 302 furthermore has a brush system 322 and extinguishing systems 324.

The computer system 304 is used to control the processes taking place in the testing device 300, and therefore comprises software 326 for regulating the process operations. The computer system 304 is also used to evaluate the measurement results obtained from specimens by means of the testing chamber 302, and therefore comprises software 328 for evaluating the measurement results. The software 328 is also used to compile a test report 330 from the measurement results which are obtained, as is provided according to the standards EN 60695-2-12 and -13.

The sample magazine 306 comprises a storage unit for specimens 332, in which a multiplicity of specimens are stored. The sample magazine 306 also has a climate control system 334, which makes it possible to store the specimens according to the climatic conditions specified in the standards above. The sample magazine 306 furthermore comprises transport means 336, by means of which a specimen can respectively be transported from the storage unit 332 to the testing chamber 302.

There, the thickness of the specimen is determined by means of the thickness measuring system 316 and the specimen is fixed in the holding device 314. After the glow wire 308 has reached a temperature predetermined by the computer system 304, the specimen fixed in the holding device 314 is brought in contact with the glow wire 308 so that, if applicable, ignition of the specimen or wrapping tissue can be detected by means of the camera system 312 and by means of the computer system 304, as described above.

The feed and positioning system for wrapping tissue 320 is used after a test has been carried out for a specimen, in particular after the wrapping tissue placed underneath has ignited, in order to replace the wrapping tissue with new wrapping tissue which is taken from the wrapping tissue roll container 318. The glow wire 308 may furthermore be cleaned by means of the brush system 322 to remove residues of the specimen remaining on the glow wire. The extinguishing system 324 is used to extinguish a burning specimen, or burning wrapping tissue.

FIG. 4 shows an image of an embodiment of the testing chamber 400. The testing chamber 400 comprises a glow wire 402 and a holding device 404 for a specimen (not shown here). The specimen is located in particular behind that region of the holding device 404 which is visible here. The specimen is taken essentially in a horizontal position through an opening 406 from a feed system. The holding device 404 is tiltable, so that the specimen can essentially be aligned vertically.

The glow wire 402 can be moved in the direction of the specimen arranged in the holding device 404.

The specimen can be observed by means of the camera system 410. The testing chamber 400 furthermore has brushes 408, which can be moved onto the glow wire and by means of which residues of the specimen can be removed from the glow wire 402. The testing chamber 400 also has a nitrogen line 412 with a nitrogen nozzle at its end, in order to extinguish a burning specimen in the holding device 404.

LIST OF REFERENCES

100 Device
102 Testing chamber
104 Computer system
106 Glow wire
108 Frame for glow wire
110 Glow wire heater
112 Holding device
114 Fixing means
116 Specimen
118 Surface
120 Force and displacement transducer
122 Camera system
124 Camera system
126 Camera system
128 Wrapping tissue
130 Microprocessor
132 Memory
134 Monitor
136 Interfaces
138 Computer program product
140 Temperature
142 Contact time
144 Image data
146 Reference
148 Reference image
150 Measurement scale
152 Region
154 Flame height
156 First duration
158 Second duration
160 Observation time
300 Testing device 302 Testing chamber
304 Computer system
306 Sample Magazine
308 Glow wire
310 Glow wire heater
312 Camera systems
314 Holding device
316 Thickness measuring system
318 Wrapping tissue roll container
320 Feed and positioning system for wrapping tissue
322 Brush system
324 Extinguishing systems
326 Software
328 Software
330 Test report
332 Storage unit
334 Climate control system
336 Transport means
400 Testing chamber
402 Glow wire
404 Holding device
406 Opening
408 Brushes
410 Camera system
412 Nitrogen line

The invention claimed is:

1. Method for testing the fire hazard of a material, the method comprising:
   bringing a plane region of a surface of a specimen in contact with a glow wire with a predetermined force for at most a predetermined contact time, the specimen consisting of said material, a tip of the glow wire being applied approximately on the middle of the plane region, the glow wire being at a predetermined temperature,
   acquiring image data of the specimen with at least a first camera at least while the specimen is in contact with the glow wire, and
   image-processing the acquired image data of the specimen, ignition of the specimen by the glow wire being detected if applicable, a first duration being determined, the first duration corresponding to the length of time between the application of the tip of the glow wire on the specimen and the start of ignition of the specimen while the specimen is in contact with the glow wire.

2. Method according to claim 1, further comprising:
   storing the first duration,
   image-processing the acquired image data of the specimen, an end of the ignition of the specimen being detected after a second duration if applicable, the second duration corresponding to the length of time between the application of the tip of the glow wire on the specimen and the end of the ignition of the specimen, and
   storing the second duration.

3. Method according to claim 1 or 2, wherein the contact between the specimen and the glow wire is ended after a predetermined contact time has elapsed, the acquisition of image data of the specimen by at least the first camera also being carried out for a predetermined observation time after the contact time has elapsed.

4. Method according to claim 3, wherein, if applicable, the ignition of the specimen is extinguished either after the ignition has been detected or after the observation time has elapsed.

5. Method according to claim 1, wherein the region of the specimen, where the glow wire is located, is not employed by the image processing in order to determine whether there is ignition of the specimen.

6. Method according to claim 3, further comprising:
   image-processing the image data of the specimen in order to detect whether burning threads are pulled from the specimen at the end of the contact time with the glow wire and whether the burning threads ignite the specimen, and
   extinguishing the burning threads on the glow wire if applicable.

7. Method according to claim 1, wherein the acquired image data of the specimen are compared with a reference image of the specimen, ignition of the specimen being detected if the colors of at least parts of the specimen are different from the corresponding colors of the parts in the reference image.

8. Method according to claim 1, further comprising:
   determining a height of any flames of the ignited specimen, if applicable, by the image-processing of the acquired image data of the ignited specimen, and
   storing the height of the flames.

9. Method according to claim 1, further comprising:
   positioning wrapping tissue in a region below where the glow wire and the specimen come in contact,
   acquiring image data of the wrapping tissue with at least a second camera at least while the specimen is in contact with the glow wire,
   image-processing the acquired image data of the wrapping tissue, ignition of the wrapping tissue being detected if applicable, a third duration being determined, the third duration corresponding to the length of time between the application of the tip of the glow wire on the specimen and the ignition of the wrapping tissue,
   storing the third duration if applicable, and
   extinguishing the wrapping tissue if applicable.

10. Method according to claim 1, further comprising:
    determining a penetration depth of the glow wire through the specimen, and
    storing the penetration depth.

11. Method according to claim 1, wherein the specimen is designed in the form of a disc or plate, a holding device being used to bring the specimen to the glow wire, the specimen being fixed with a surface essentially aligned horizontally in the holding device, the holding device having a tilting mechanism, the holding device being tiltable essentially through 90° by the tilting mechanism, the surface with the plane region essentially being aligned vertically by the tilting of the holding device.

12. Computer program product having computer-executable instructions for carrying out the method of claim 1.

13. Device for testing the fire hazard of a material, the device comprising:
    means for bringing a plane region of the surface of a specimen in contact with a glow wire with a predetermined force for at most a predetermined contact time, the specimen consisting of said material, a tip of the glow wire being applied approximately on the middle of the plane region, the glow wire being at a predetermined temperature,
    means for acquiring image data of the specimen with at least a first camera at least while the specimen is in contact with the glow wire, and
    means for image-processing the acquired image data of the specimen, ignition of the specimen by the glow wire being detected if applicable, a first duration being determined, the first duration corresponding to the length of time between the application of the tip of the glow wire on the specimen and the start of ignition of the specimen while the specimen is in contact with the glow wire.

14. Device according to claim 13, further comprising:
means for storing the first duration,
means for image-processing the acquired image data of the specimen, an end of the ignition of the specimen being detected after a second duration if applicable, the second duration corresponding to the length of time between the application of the tip of the glow wire on the specimen and the end of the ignition of the specimen, and
means for storing the second duration.

15. Device according to one of the preceding claim 13 or 14, further comprising:
means for image-processing the image data of the specimen in order to detect whether burning threads are pulled from the specimen at the end of the contact with the glow wire and whether the burning threads ignite the specimen,
means for extinguishing the burning threads on the glow wire, and
means for extinguishing the ignited specimen.

16. Device according to claim 13, further comprising:
means for positioning wrapping tissue in a region below where the glow wire and the specimen come in contact,
means for acquiring image data of the wrapping tissue with at least a second camera at least while the specimen is in contact with the glow wire,
means for image-processing the acquired image data of the wrapping tissue, ignition of the wrapping tissue being detectable if applicable, a third duration being determinable, the third duration corresponding to the length of time between the application of the tip of the glow wire on the specimen and the ignition of the wrapping tissue, and
means for storing the third duration if applicable, means for extinguishing the wrapping tissue if applicable.

17. Device according to claim 13, further comprising a holding device for bringing the specimen to the glow wire, the specimen being designed in the form of a disc or plate, the specimen being fixable with a surface essentially aligned horizontally in the holding device, the holding device having a tilting mechanism, the holding device being tiltable essentially through 90° by the tilting mechanism, the surface with the plane region essentially being alignable vertically by the tilting of the holding device.

* * * * *